(12) United States Patent
Tokudome et al.

(10) Patent No.: US 6,878,548 B2
(45) Date of Patent: Apr. 12, 2005

(54) COMPOSITION FOR USE IN ELECTROPORATION

(75) Inventors: Yoshihiro Tokudome, Yokohama (JP); Toshihiro Hinokitani, Yokohama (JP); Kenichi Goto, Yokohama (JP); Kenji Sugibayashi, Kawagoe (JP); Koji Owaku, Yokohama (JP); Yasunori Inaoka, Yokohama (JP)

(73) Assignee: Pola Chemical Industries Inc., Shizuoka (JP)

( * ) Notice: Subject to any disclaimer, the term of this patent is extended or adjusted under 35 U.S.C. 154(b) by 0 days.

(21) Appl. No.: 10/467,971

(22) PCT Filed: Feb. 19, 2002

(86) PCT No.: PCT/JP02/01425

§ 371 (c)(1),
(2), (4) Date: Aug. 13, 2003

(87) PCT Pub. No.: WO02/066003

PCT Pub. Date: Aug. 29, 2002

(65) Prior Publication Data

US 2004/0071763 A1 Apr. 15, 2004

(30) Foreign Application Priority Data

Feb. 19, 2001 (JP) .................................. 2001-041187

(51) Int. Cl.[7] .............................................. C12N 15/64

(52) U.S. Cl. ........................ 435/461; 435/470; 435/471; 435/285.2

(58) Field of Search .................................. 435/461, 470, 435/471, 285.2

(56) References Cited

U.S. PATENT DOCUMENTS 5,231,019 A * 7/1993 Paszkowski et al. ........ 435/470

FOREIGN PATENT DOCUMENTS

| JP | 06-335332 | 12/1994 |
| WO | WO 89/06555 | 7/1989 |

OTHER PUBLICATIONS

CRC Handbook of Chemistry and Physics, 60th ed., CRC Press, Inc., Boca Raton, Florida, 1979, pp. D–227, D–231, D–233 and D–244.*

* cited by examiner

Primary Examiner—James Ketter
(74) Attorney, Agent, or Firm—Knobbe, Martens, Olson & Bear LLP

(57) ABSTRACT

The present invention is a composition for percutaneous administration suitable for electroporation. Percutaneous absorption of a drug and so forth in a composition for electroporation can be promoted by adding alkaline earth metal ions to the composition.

10 Claims, 11 Drawing Sheets

COMPOSITION FOR USE IN ELECTROPORATION

RELATED APPLICATIONS

This application is the U.S. National Phase under 35 U.S.C. § 371 of International Application PCT/JP02/01425, filed Feb. 19, 2002, which was published in language other than English, which claims priority of Japanese Patent Application No. 2001-41187, filed on Feb. 19, 2001. Each of the above applications are incorporated herein by reference in their entirety.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Technical Field

The present invention relates to a composition for electroporation useful for improving percutaneous absorption of drugs or the like.

2. Background Art

Since percutaneous absorption as an administration route gives less pain compared with injection or the like and shows lower incidence of forgetting administration compared with oral administration, it is expected as a promising drug administration route. However, percutaneous absorption is difficult due to the inherent defense function of skin and, thus it has not been established yet as means for drug delivery. As an example of methods proposed to overcome such a current problem, there can be mentioned the so-called electroporation, in which pores are formed in the skin structure by applying a voltage so that a drug should be transported through the pores. It has been recently becoming clear that the drug behavior is different in such electroporation from those in usual administrations, and development of compositions for percutaneous administration suitable for such electroporation has been desired. That is, although electroporation is useful means for percutaneous drug transport, this technique alone may not be sufficient for drug transport, and thus development of pharmaceutical preparations that enhance that effect has been desired.

Meanwhile, no composition for electroporation containing alkaline earth metal ions such as calcium ions is known. It is not known either that the presence of alkaline earth metal ions promote percutaneous drug absorption by electroporation.

DISCLOSURE OF THE INVENTION

An object of the present invention is to provide a composition for percutaneous administration suitable for electroporation.

The inventors of the present invention assiduously studied to obtain a composition for percutaneous administration suitable for electroporation. As a result, they found that percutaneous absorption of active ingredients in a composition for electroporation could be promoted during electroporation by adding alkaline earth metal ions such as calcium ions to the composition, and thus accomplished the present invention. The present invention thus relates to the following techniques.

(1) A composition for electroporation, which contains alkaline earth metal ions and a carrier for electroporation.
(2) The composition for electroporation according to (1), wherein the alkaline earth metal ions are calcium ions, barium ions or magnesium ions.
(3) The composition for electroporation according to (1) or (2), wherein the alkaline earth metal ions are contained in the form of chloride, and at least a part of the alkaline earth metal ions exist in the form of ions.
(4) The composition for electroporation according to any one of (1) to (3), wherein the alkaline earth metal ions are contained at a concentration of 50 to 600 mM in terms of a molar concentration of an alkaline earth metal salt.
(5) The composition for electroporation according to any one of (1) to (4), which is used for pharmaceuticals.
(6) An administration unit for a composition for electroporation of a drug for external use, which comprises a device for electroporation and the composition for electroporation according to (5).

Hereafter, the present invention will be explained in detail with reference to the following examples.

(1) Alkaline Earth Metal Ions Used in Composition for Electroporation of the Present Invention The composition for electroporation of the present invention contains alkaline earth metal ions such as calcium ions as essential ingredients. Examples of the alkaline earth metal ions include calcium ions, magnesium ions, barium ions, strontium ions and so forth. Among these, calcium ions and barium ions are preferred, and calcium ions are particularly preferred, in view of safety, versatility and effect. Such alkaline earth metal ions as calcium ions are preferably added to the composition for electroporation of the present invention in the form of water-soluble alkaline earth metal salts. Preferred examples of the water-soluble alkaline earth metal salts include, for example, chlorides, nitrates and so forth. One kind of such salts can be solely added, or two or more kinds thereof can be added in combination. It is particularly preferable to add them in the form of chloride salts. At least a part of the alkaline earth metal salts contained in the composition for electroporation of the present invention exist in a state of ions in the composition. The expression of "at least a part" means an amount sufficient for increasing percutaneous absorption of a drug. In the composition for electroporation of the present invention, the concentration of such alkaline earth metal ions in the form of salts is preferably 10 to 1000 mM, more preferably 50 to 600 mM, particularly preferably 100 to 300 mM, in terms of the molar concentration of the salts. This is because a concentration in such a range particularly promotes the percutaneous absorption of active ingredients contained in the composition.

(2) Composition for Electroporation of the Present Invention

The composition for electroporation of the present invention can contain arbitrary ingredients usually used in compositions for electroporation for the production of pharmaceutical preparations. Preferred examples of such arbitrary ingredients include hydrocarbons such as squalane, vaseline and microcrystalline wax, esters such as jojoba oil, carnauba wax and octyldodecyl oleate, triglycerides such as olive oil, beef tallow and coconut oil, fatty acids such as stearic acid, oleic acid and ricinoleic acid, higher alcohols such as oleyl alcohol, stearyl alcohol and octyldodecanol, anionic surfactants such as sulfosuccinic acid esters and sodium polyoxyethylenealkylsulfates, amphoteric surfactants such as alkyl betaine salts, cationic surfactants such as dialkylammonium salts, nonionic surfactants such as sorbitan fatty acid esters, fatty acid monoglycerides, polyoxyethylene adducts thereof, polyoxyethylene alkyl ethers and polyoxyethylene fatty acid esters, thickening/gelling agents, antioxidants, ultraviolet absorbers, coloring materials, preservatives and powders, ingredients for promoting percutaneous absorption including polyhydric alcohols such as 1,3-butanediol, propylene glycol and glycerin, monoterpenes such as menthol and thymol, ingredients for controlling percutaneous absorption patterns including phospholipids such as lecithin, phosphatidylglycerol and phosphatidylethanolamine, and so forth. One kind of such arbitrary ingredients can be solely added, or two or more kinds thereof can be added in combination.

Further, drugs to be percutaneously administered by electroporation are not particularly limited so long as they are usually used as drugs. Preferred examples thereof include analgesic/antipyretic/antiphlogistic agents such as codeine, morphine, hydromorphone, oxycodone, pethidine, buprenorphine hydrochloride, pentazocine and tramadol hydrochloride, protein drugs such as insulin, calcitonin, elcatonin, adrenocorticotropic hormone (ACTH), parathyroid hormone (PTH), selectin, oxytocin, angiotensin, $\beta$-endorphin, vasopressin, glucagon, somatostatin, luteinizing hormone-releasing hormone (LH-RH), enkephalin, neurotensin, atrial natriuretic polypeptide (ANP), growth hormone, bradykinin, substance P, dynorphin, thyroid-stimulating hormone (TSH), prolactin, erythropoietin, G-CSF, glutathione peroxidase, superoxide dismutase (SOD), desmopressin, somatomedin, melanocyte-stimulating hormone (MSH), calcitonin gene related peptide (CGRP), endothelin and thyrotropin-releasing hormone (TRH), interleukins, interferons, antiplatelet drugs, vasodilators, anti-arteriosclerosis drugs including argatroban, sarpogrelate hydrochloride, beraprost sodium, limaprost alfadex and cilostazol, antiallergic agents such as azelastine hydrochloride, antiussive expectorant drugs such as tipepidine hibenzate and so forth. Among these, analgesic drugs such as buprenorphine hydrochloride are particularly preferred. This is because these drugs are required to be serially administered in a required amount in a time course, and the characteristics of percutaneous administration are suitable for this requirement. Further, one kind of such drugs can be solely added, or two or more kinds thereof can be added in combination, to the composition.

The composition for electroporation of the present invention can be made into a preparation form suitable for physicochemical properties of the active ingredients such as solution, emulsion, semisolid and solid by treating the aforementioned essential ingredients, preferred ingredients, arbitrary ingredients and active ingredients according to a usual method and used for percutaneous administration of the active ingredients together with a device for electroporation. Among these, examples of the preferred pharmaceutical preparation include aqueous preparations, and aqueous solution preparations, aqueous gel preparations, emulsion preparations and so forth are particularly preferred. The composition for electroporation of the present invention is a composition containing alkaline earth metal ions and a carrier for electroporation. The carrier for electroporation is a carrier for formulating such preparations for electroporation as described above, and particularly preferred examples thereof include aqueous solvents, gelling agents, emulsifiers and so forth.

The composition of the present invention is a composition for external use, since it is characterized by being used for electroporation. The compositions for external use may be cosmetic compositions or pharmaceutical compositions. However, pharmaceutical compositions are particularly preferred, since they can fully exhibit the effect by their characteristic of significantly promoting percutaneous absorption.

(3) Administration Unit for Drug for External Use of the Present Invention

The administration unit for a drug for external use of the present invention comprises the aforementioned pharmaceutical composition for electroporation of the present invention and a device for electroporation. The device for electroporation is not particularly limited so long as it is a device usually used for the aforementioned purpose. For example, the devices described in International Patent Unexamined Publication in Japanese (KOHYO) Nos. 11-507341, 11-505445, 10-502827, 11-503349, 08-511680, 03-502416 and so forth can be used. Further, examples of such devices for electroporation that are commercially available include ECM-600 produced by BTX and GENE PULSER produced by BIO-RAD, which are exponential decay-type pulse generators, and ECM-830 produced by BTX, which is a square-type pulse generator, and these devices can also be used. Electroporation can be performed according to conventionally known conditions, and the conditions can also be appropriately changed.

BRIEF DESCRIPTION OF THE DRAWINGS

FIG. 6 shows the total amount of percutaneous absorption observed in Example 8.

BEST MODE FOR CARRYING OUT THE INVENTION

Hereafter, the present invention will be explained more specifically with reference to the following examples. However, it is apparent that the scope of the present invention is not limited to these examples.

EXAMPLES 1 to 3

Figure 1:
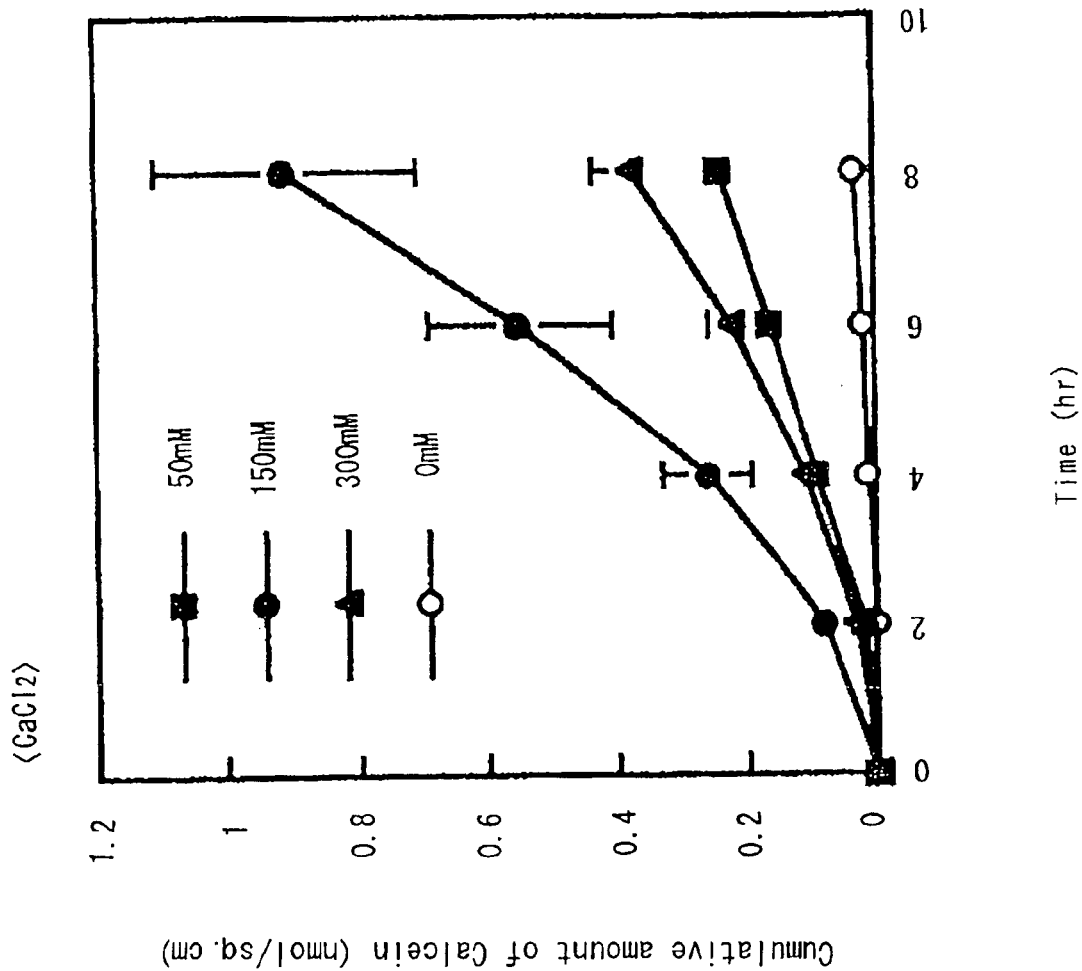
FIG. 1 shows percutaneous absorption promotion actions observed in Examples 1 to 3.
Figure 2:
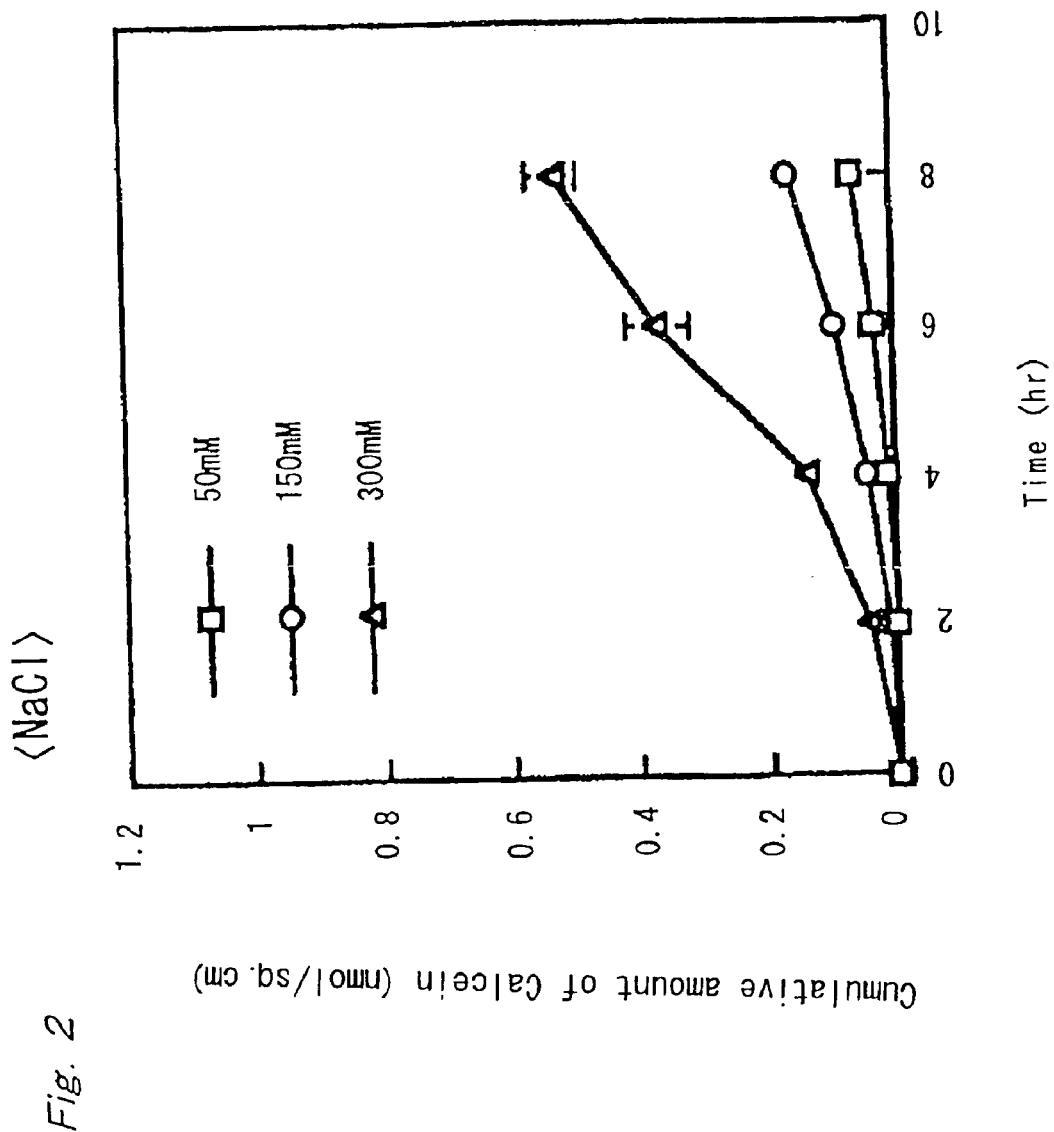
FIG. 2 shows effect of the addition of sodium chloride as comparative examples of Examples 1 to 3.

The compositions for electroporation of the present invention were produced according to the prescriptions shown in Table 1 mentioned below. Calcein sodium salt was used as a model labeled drug at a concentration of 1 mM. The ingredients were stirred and solubilized to obtain the compositions for electroporation (solutions) of the present invention. The percutaneous absorption promotion actions of these compositions for electroporation were measured by percutaneous permeability test using a Franz cell. That is, a skin sample was collected from the abdomen of a hairless rat, and subcutaneous fat was removed from the sample. The skin sample was loaded in the Franz cell as a partition wall with its horny cell layer facing towards the donor side. The receiver side was filled with an isotonic phosphate-buffered saline (PBS). The donor side was filled with 3 mL of the aforementioned composition for electroporation of the present invention. The receiver side was stirred at 1200 rpm by using a star-head type stirrer. After the electroporation, 0.3 mL of the solution in the receiver side was serially collected in a time course and added with the same amount of isotonic phosphate-buffered saline (PBS) to examine the percutaneous permeability. As a control example, a composition that did not contain calcium chloride was used. As comparative examples, compositions in which sodium chloride was substituted for calcium chloride were used. The amount of calcein sodium salt was measured by a fluorometer. Further, as for the conditions of electroporation, ECM-830 produced by BTX was used, 10 pulses of 10 ms at 300 V was applied at intervals of 1 minute immediately after the drug administration, and then the power was turned off. The results of the addition of calcium chloride are shown in FIG. 1. The results of the addition of sodium chloride are shown in FIG. 2. These results show that the existence of calcium chloride markedly promoted percutaneous absorption of calcein, and that this percutaneous absorption promotion action is effect of calcium ions.

TABLE 1

| Example | Prescription |
| --- | --- |
| Example 1 | Calcium chloride: 50 mM |
|  | Calcein: 1 mM |
|  | Water: Remainder |
| Example 2 | Calcium chloride: 150 mM |
|  | Calcein: 1 mM |
|  | Water: Remainder |
| Example 3 | Calcium chloride: 300 mM |
|  | Calcein: 1 mM |
|  | Water: Remainder |

EXAMPLES 4 to 7

Figure 3:
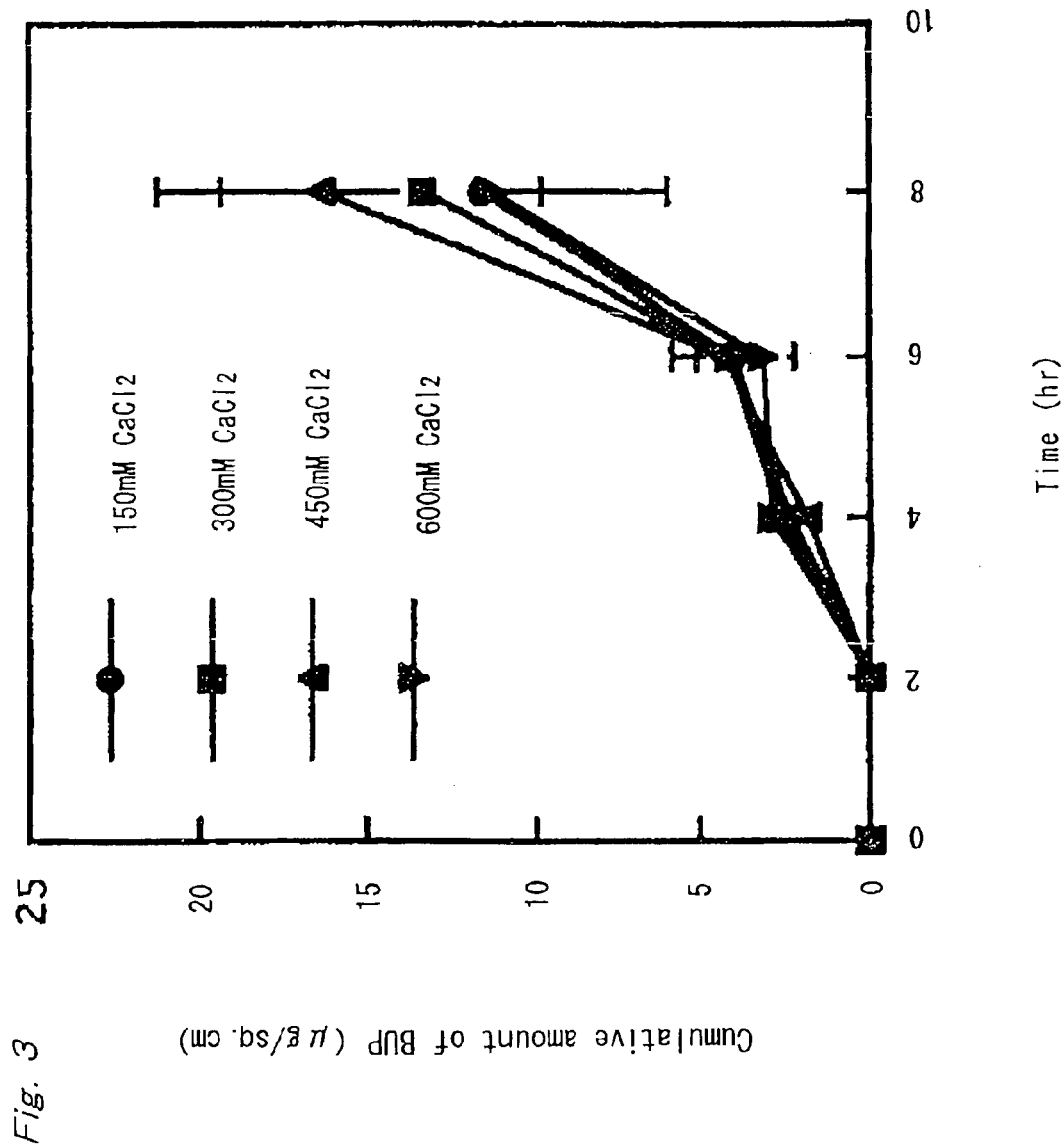
FIG. 3 shows changes of absorption with time observed in Examples 4 to 7.
Figure 4:
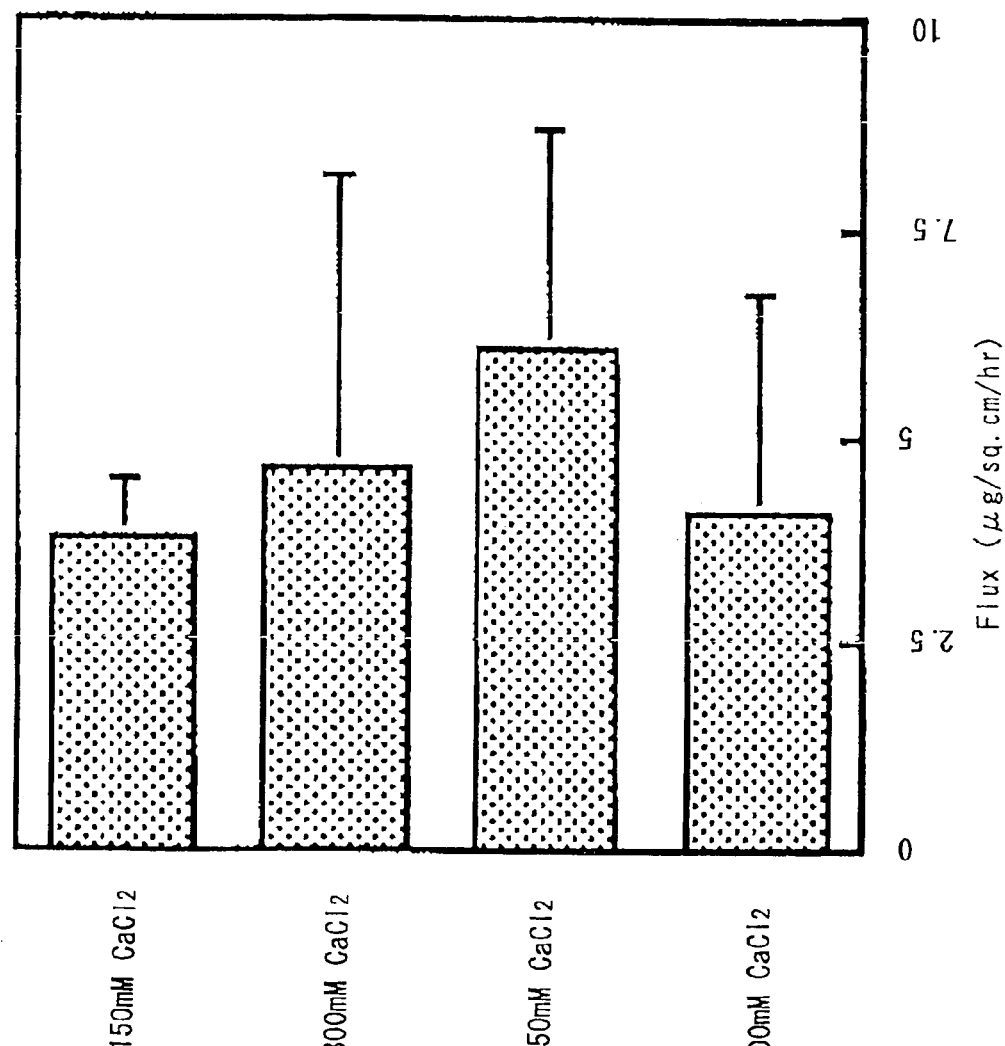
FIG. 4 shows the total amounts of percutaneous absorption observed in Examples 4 to 7.

Compositions for electroporation were produced according to the prescriptions shown in Table 2 mentioned below in the same manner as in the above examples to examine the percutaneous permeability in the same manner as in the above examples. The results are shown in FIGS. 3 and 4. These results show that it is appropriate to add 10 to 1000 mM, more preferably 50 to 600 mM, further preferably 300 to 500 mM, of calcium ions in terms of calcium chloride to the composition of the present invention.

TABLE 2

| Sample | Prescription |
| --- | --- |
| Example 4 | Buprenorphine hydrochloride: 0.02% by weight |
|  | Calcium chloride: 150 mM |
|  | Water: Remainder |
| Example 5 | Buprenorphine hydrochloride: 0.02% by weight |
|  | Calcium chloride: 300 mM |

TABLE 2-continued

| Sample | Prescription |
| --- | --- |
|  | Water: Remainder |
| Example 6 | Buprenorphine hydrochloride: 0.02% by weight |
|  | Calcium chloride: 450 mM |
|  | Water: Remainder |
| Example 7 | Buprenorphine hydrochloride: 0.02% by weight |
|  | Calcium chloride: 600 mM |
|  | Water: Remainder |

EXAMPLE 8

Figure 5:
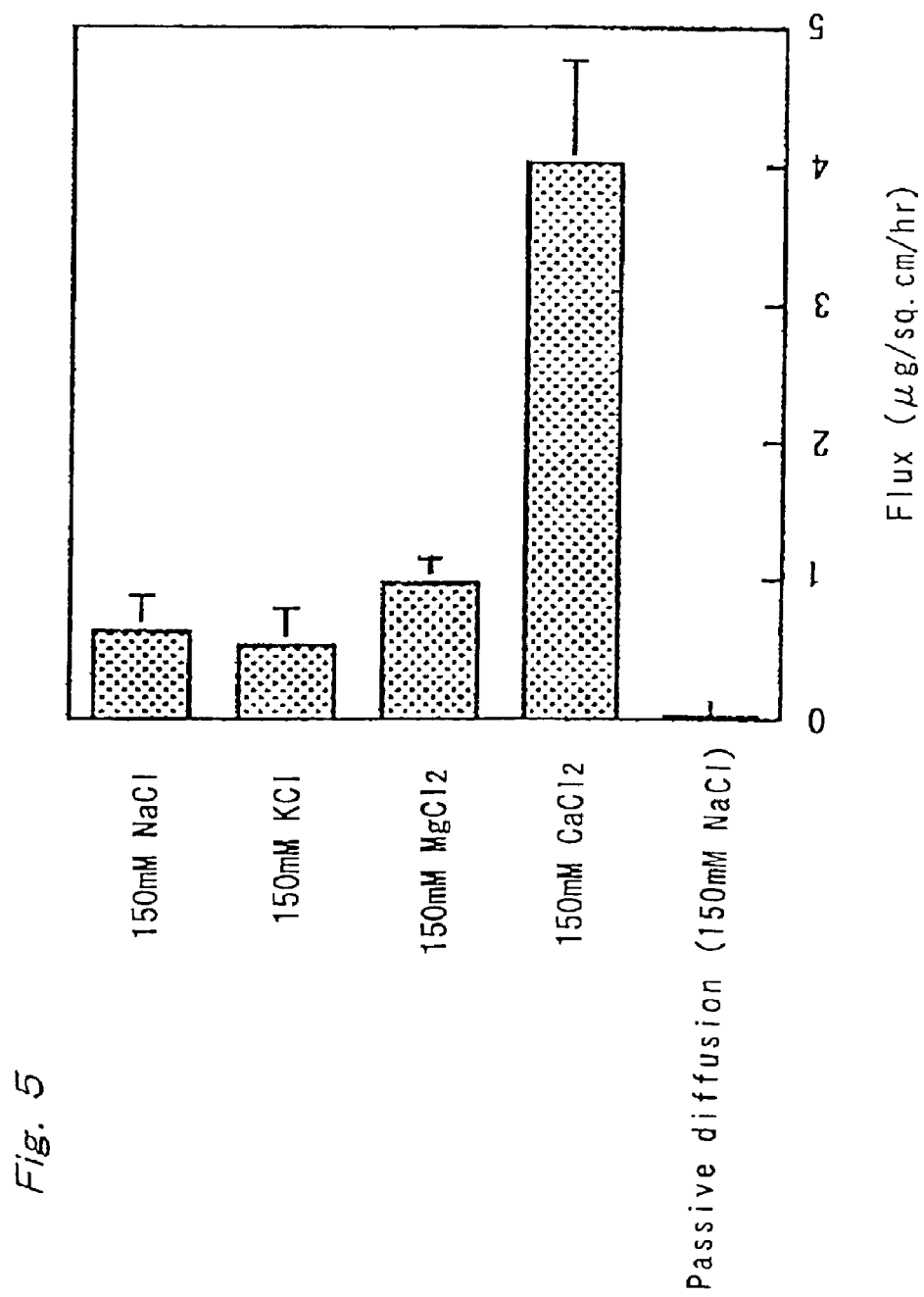
FIG. 5 shows changes of absorption with time observed in Example 8.

The percutaneous absorption promotion action was compared for the sample of Example 4 with changing the metal chloride to other metal chlorides such as sodium chloride, potassium chloride and magnesium chloride. The concentrations of these salts added were all 150 mM, which was the same as that of calcium chloride in Example 4. The results are shown in FIGS. 5 and 6. These results show that, although the additions of all the metal ions promoted percutaneous absorption, the addition of calcium ions particularly markedly promoted the action, and thus the specificity of calcium ions was confirmed.

EXAMPLE 9

Figure 7:
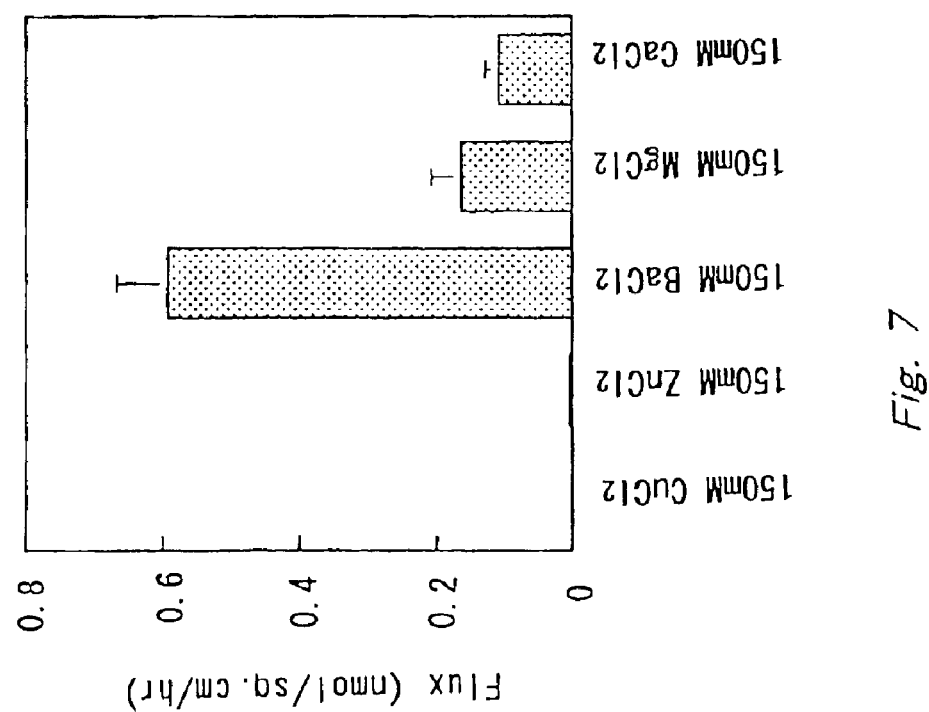
FIG. 7 shows effect of divalent ions on percutaneous absorption of calcein by electroporation observed in Example 9.

The same examination as in Example 1 was conducted by using various metal chlorides. As the metal chlorides, copper chloride, zinc chloride, barium chloride, magnesium chloride and calcium chloride were used. The results are shown in FIG. 7. These results show that the additions of barium chloride, calcium chloride and magnesium chloride promoted the absorption of calcein during electroporation.

EXAMPLE 10

Figure 8:
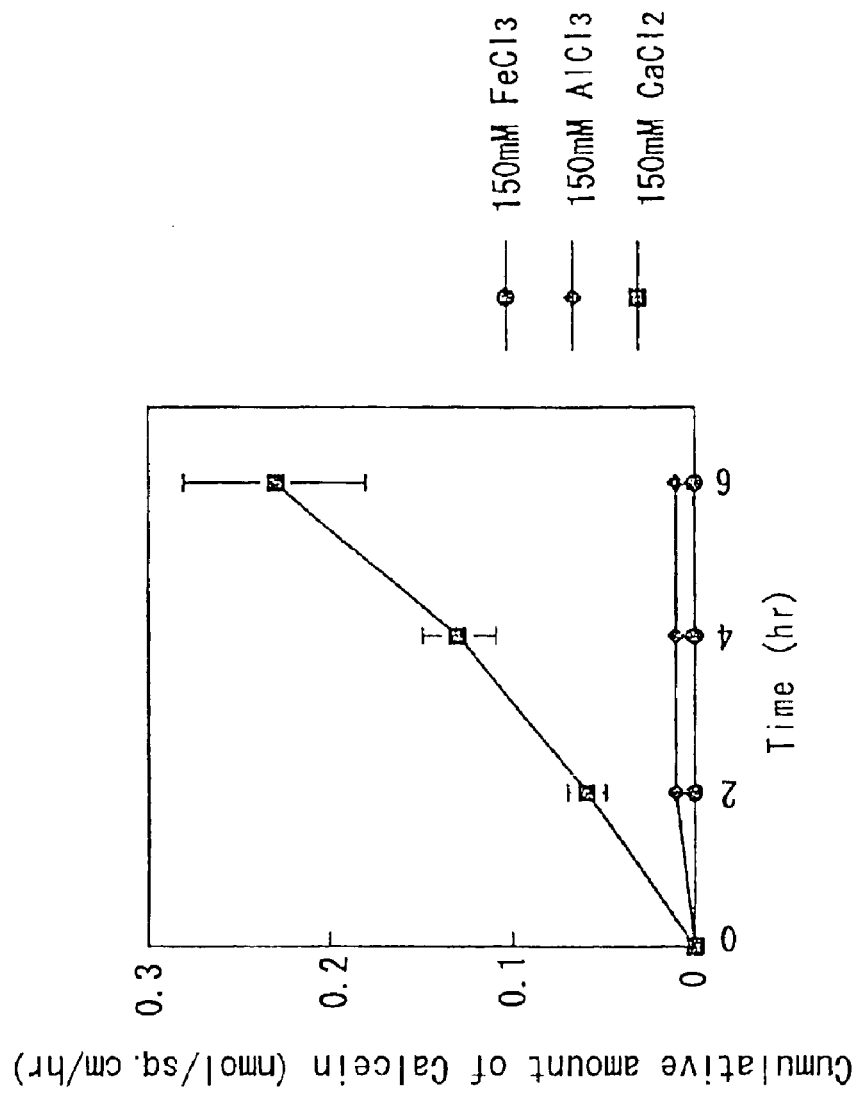
FIG. 8 shows effect of trivalent ions on percutaneous absorption by electroporation observed in Example 10.
Figure 9:
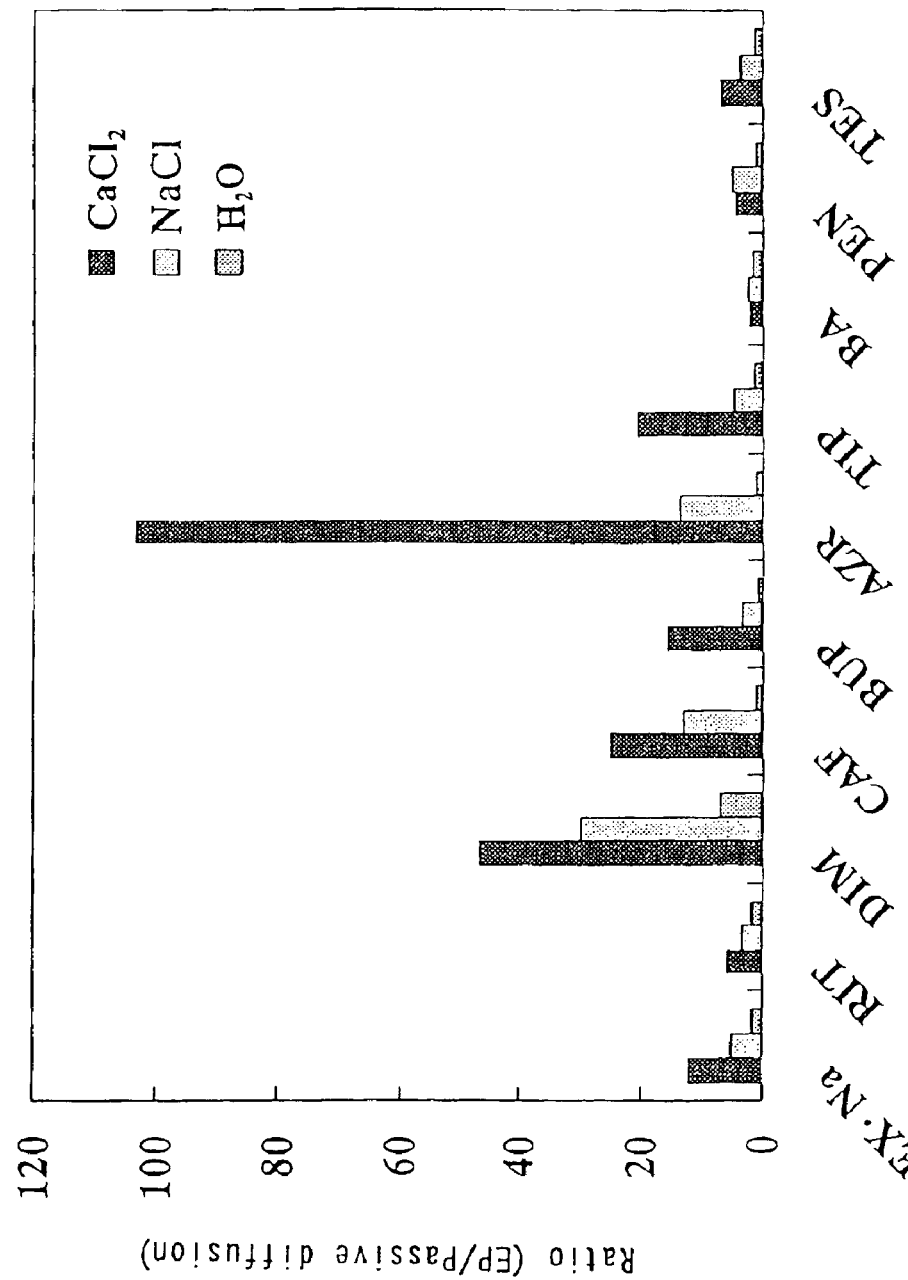

The same examination as in Example 1 was conducted by using trivalent metal ion chlorides. As for the electroporation conditions, 10 pulses of 10 ms at 300 V were applied at intervals of 1 second immediately after the drug administration. As the trivalent metal ion chlorides, iron chloride and aluminum chloride were used. The results are shown in FIG. 8. These results show that neither of the trivalent metal ions significantly promoted percutaneous absorption. To the contrary, it was confirmed that the addition of calcium ions significantly promoted percutaneous absorption.

EXAMPLE 11

Figure 9:
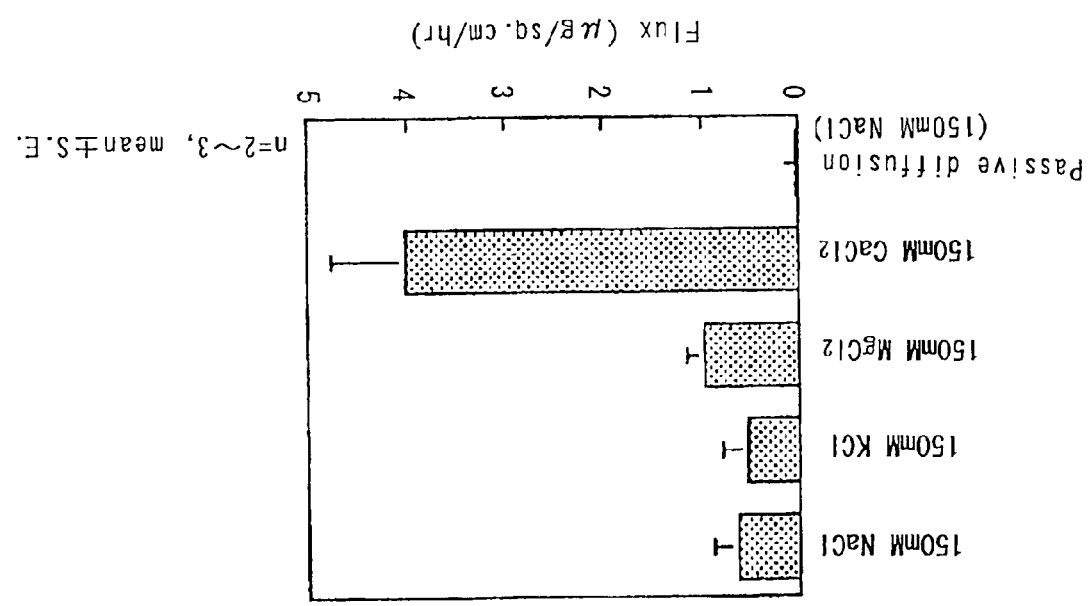
FIG. 9 shows electroporation promotion effect by the addition of $CaCl_2$ observed in Example 11.

The same examination as in Example 1 was conducted by using various drugs as model labeled drugs. However, dorsal skin of a hairless rat was used as the skin sample. Further, as for the electroporation condition, 10 pulses of 10 ms at 300 V were applied at intervals of 1 second immediately after the drug administration. As the model labeled drugs, sodium dexamethasone phosphate (DEX.Na), ritodrine hydrochloride (RIT), dimemorfan phosphate (DIM), caffeine (CAF), azelastine hydrochloride (AZR), tipepidine hibenzate (TIP), benzoic acid (BA), phenytoin (PEN) and testosterone (TES) were used. The results are shown in FIG. 9. From these results, it was confirmed that the addition of calcium ions significantly promoted percutaneous absorption of azelastine hydrochloride (AZR) and tipepidine hibenzate (TIP).

EXAMPLE 12

Figure 10B:
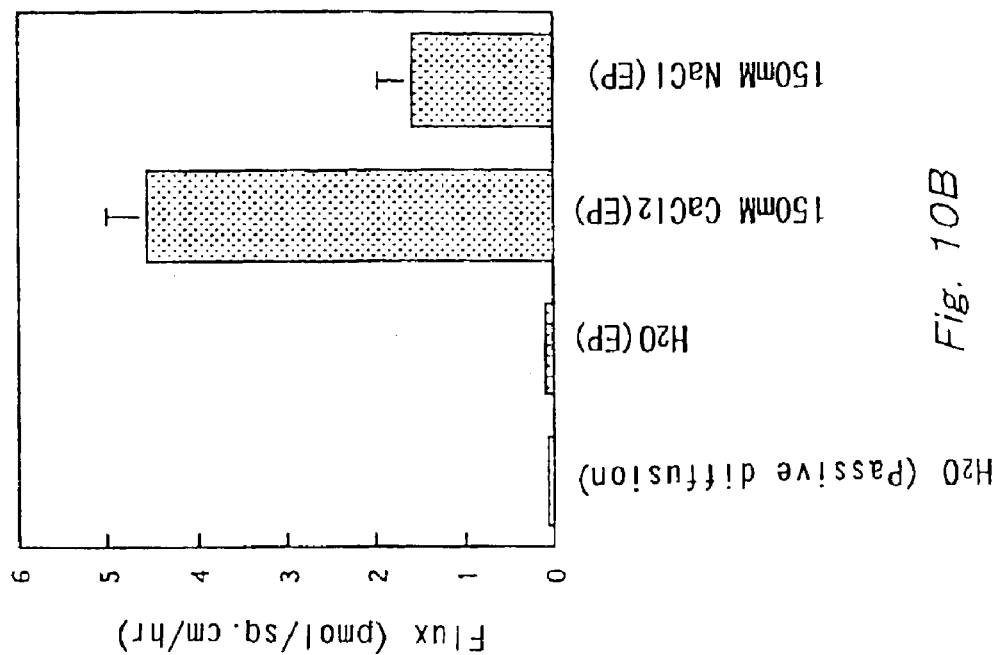
FIG. 10 shows the results of mechanism analysis of percutaneous absorption promotion effect by electroporation performed in Example 12. A represents the examination using FD4 (M.W. 4300). B represents the examination using FD10 (M.W. 9600). C represents the examination using FD40 (M.W. 35600).
Figure 10A:
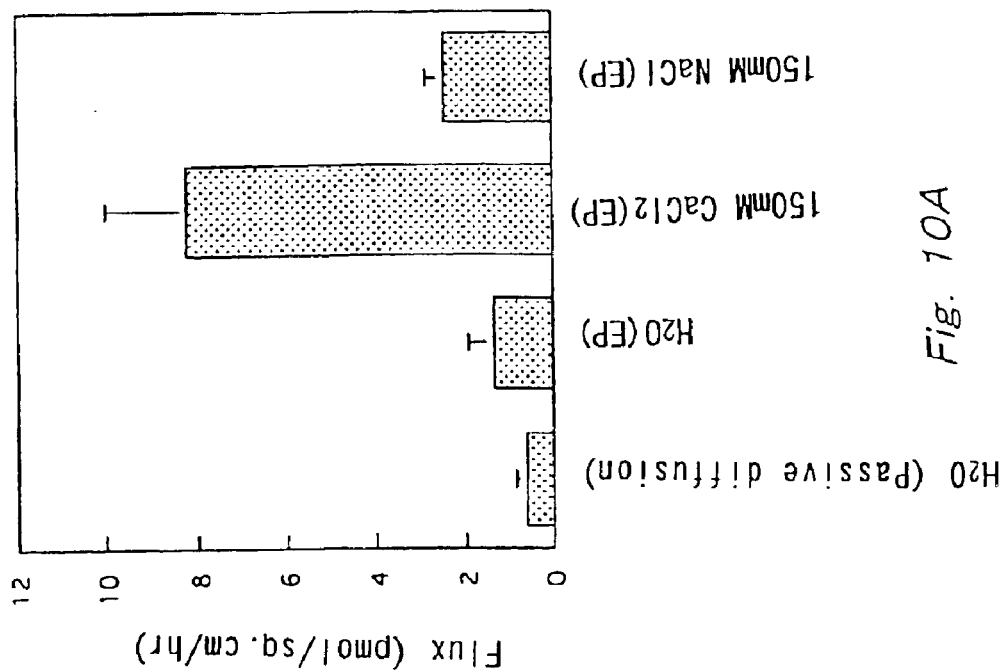
Figure 10C:
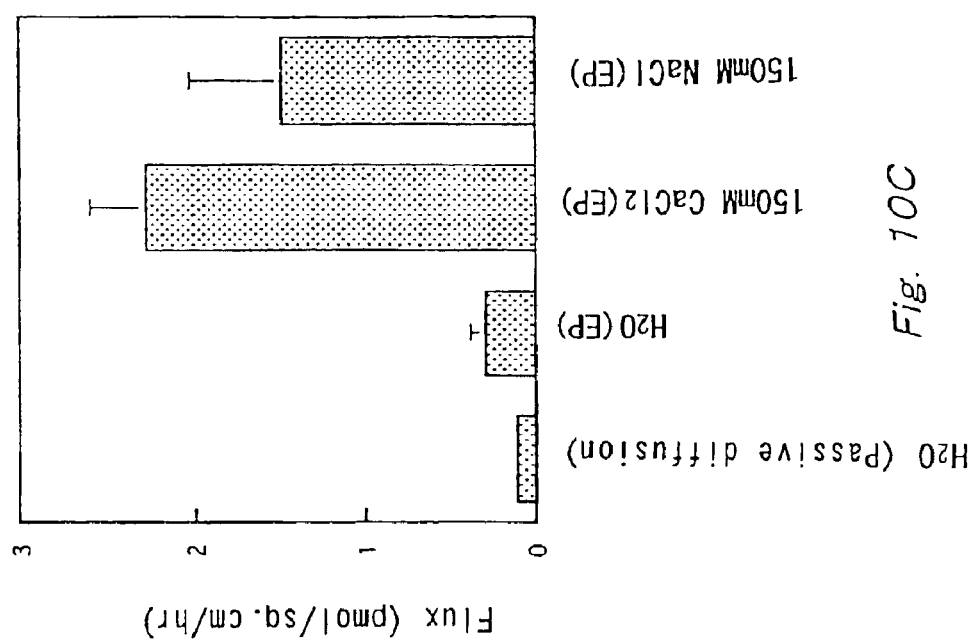

The same examination as in Example 1 was conducted by using FITC-dextran as a model labeled drug. As for the electroporation conditions, 10 pulses of 10 ms at 300 V were applied at intervals of 1 second immediately after the drug administration. As the FITC-dextran, FD4 (molecular weight: 4300), FD10 (molecular weight: 9600) and FD40 (molecular weight: 35600) were used. The results are shown in FIG. 10. From these results, it was confirmed that the addition of calcium ions significantly promoted percutaneous absorption of FITC-dextran having any of the molecular weights.

INDUSTRIAL APPLICABILITY

According to the present invention, a composition for percutaneous administration suitable for electroporation can be provided.

What is claimed is:

1. A composition for electroporation, which comprises alkaline earth metal ions, a drug and a carrier for electroporation.

2. The composition for electroporation according to claim 1, herein the alkaline earth metal ions are calcium ions, barium ions or magnesium ions.

3. The composition for electroporation according to claim 1, wherein the alkaline earth metal ions are in the form of chloride, and at least a part of the alkaline earth metal ions exist in the form of ions.

4. The composition for electroporation according to claim 1, wherein the alkaline earth metal ions are present at a concentration of 50 to 600 mM in terms of a molar concentration of an alkaline earth metal salt.

5. The composition for electroporation according to any one of claims 1 to 4, in a pharmaceutical preparation.

6. An administration unit for a composition for electroporation of a drug for external use, which comprises a device for electroporation and a composition for electroporation, which comprises alkaline earth metal ions, a drug and carrier for electroporation.

7. A method for improving percutaneous absorption of a drug, comprising the steps of:

applying a composition which comprises alkaline earth metal ions, a drug and a carrier for electroporation to skin; and applying electric current to the skin.

8. The method according to claim 7, wherein the alkaline earth metal ions are calcium ions, barium ions, or magnesium ions.

9. The method according to claim 7, wherein the alkaline earth metal ions are in the form of a chloride, and at least a part of the alkaline earth metal ions exist in the form of ions.

10. The method according to claim 7, wherein the alkaline earth metal ions are present at a concentration of 50 to 600 mM in terms of a molar concentration of an alkaline earth metal salt.

* * * * *

UNITED STATES PATENT AND TRADEMARK OFFICE
CERTIFICATE OF CORRECTION

PATENT NO. : 6,878,548 B2
DATED : April 12, 2005
INVENTOR(S) : Tokudome et al.

It is certified that error appears in the above-identified patent and that said Letters Patent is hereby corrected as shown below:

Column 1,
Line 8, "in language other" should be -- in a language other --.

Column 6,
Line 55, "phosphate (DEX.Na)," should be -- phosphate (DEX·Na), --.

Column 7,
Line 21, "herein the alkaline" should be -- wherein the alkaline --.

Column 8,
Line 8, "a drug and carrier" should be -- a drug and a carrier --.

Signed and Sealed this

Eleventh Day of April, 2006

JON W. DUDAS
*Director of the United States Patent and Trademark Office*